(12) United States Patent
Chaiyasate

(10) Patent No.: US 11,951,079 B2
(45) Date of Patent: Apr. 9, 2024

(54) TOPICAL CANNABIDIOL COMPOSITION

(71) Applicant: Kongkrit Chaiyasate, Bloomfield Hills, MI (US)

(72) Inventor: Kongkrit Chaiyasate, Bloomfield Hills, MI (US)

(*) Notice: Subject to any disclaimer, the term of this patent is extended or adjusted under 35 U.S.C. 154(b) by 41 days.

(21) Appl. No.: 17/065,818

(22) Filed: Oct. 8, 2020

(65) Prior Publication Data

US 2021/0244683 A1   Aug. 12, 2021

Related U.S. Application Data

(60) Provisional application No. 62/910,134, filed on Oct. 3, 2019.

(51) Int. Cl.
| | | |
|---|---|---|
| *A61K 31/355* | (2006.01) | |
| *A61K 9/70* | (2006.01) | |
| *A61K 31/01* | (2006.01) | |
| *A61K 31/015* | (2006.01) | |
| *A61K 31/045* | (2006.01) | |
| *A61K 31/05* | (2006.01) | |
| *A61K 36/19* | (2006.01) | |
| *A61K 36/45* | (2006.01) | |
| *A61K 36/9068* | (2006.01) | |
| *A61K 45/06* | (2006.01) | |
| *A61K 47/44* | (2017.01) | |
| *A61P 23/02* | (2006.01) | |

(52) U.S. Cl.
CPC ............ *A61K 31/05* (2013.01); *A61K 9/7023* (2013.01); *A61K 31/01* (2013.01); *A61K 31/015* (2013.01); *A61K 31/045* (2013.01); *A61K 31/355* (2013.01); *A61K 36/19* (2013.01); *A61K 36/45* (2013.01); *A61K 36/9068* (2013.01); *A61K 45/06* (2013.01); *A61K 47/44* (2013.01); *A61P 23/02* (2018.01)

(58) Field of Classification Search
CPC ....... A61K 9/0014; A61K 8/922; A61P 29/02; A61P 29/00
See application file for complete search history.

(56) References Cited

U.S. PATENT DOCUMENTS

| 10,420,802 | B2 * | 9/2019 | Taghizadeh ............ A61K 35/36 |
|---|---|---|---|
| 2012/0042420 | A1 | 2/2012 | Kaiser et al. |
| 2012/0064136 | A1 | 3/2012 | Baker, Jr. et al. |
| 2013/0184354 | A1 | 7/2013 | Jackson et al. |
| 2016/0338974 | A1 * | 11/2016 | Aung-Din ............ A61K 31/433 |
| 2018/0000727 | A1 * | 1/2018 | Willinsky ............ A61K 31/352 |
| 2018/0221392 | A1 * | 8/2018 | Chelle ..................... A61P 29/00 |
| 2018/0280274 | A1 | 10/2018 | Altman et al. |

OTHER PUBLICATIONS

Leelarungrayub, "Anti-inflammatory activity of niosomes entrapped with Plai oil (*Zingiber cassumunar* Roxb.) by therapeutic ultrasound in a rat model", International Journal of Nanomedicine, 12, pp. 2469-2476, 2017 (Year: 2017).*
Wanikiat, "The anti-inflammatory effects and the inhibition of neutrophil responsiveness by Barleria lupulina and Clinacanthus nutans extracts", Journal of Ethnopharmacology, 116, pp. 234-244, 2008 (Year: 2008).*
Medkoo (webpage at medkoo.com [retrieved on Feb. 25, 2022]. Retrieved from the Internet: <URL: https://www.medkoo.com/products/11129> (Year: 2016).*
Kumari, "Antibacterial, antioxidant and Immunomodulatory properties in extracts of Barleria lupulina Lindl.", BMC Complementary and Alternative Medicine, 17:484, pp. 1-11, 2017 (Year: 2017).*

* cited by examiner

*Primary Examiner* — Robert T. Crow
*Assistant Examiner* — John P Nguyen
(74) *Attorney, Agent, or Firm* — MaxGoLaw PLLC

(57) ABSTRACT

A topical composition and method of treating chronic pain are provided. The topical composition contains cannabidiol (CBD) and plant extract and is well suited to treat chronic pain while also avoiding the negative side effects caused by commonly used anti-inflammatory and pain-treating compounds. When the topical composition is applied to the skin at the locus of pain and allowed sufficient time to absorb, the pain is reduced or even eliminated. The topical compositions also show therapeutic effect on mucosal tissue and internal tissues of humans or animals.

18 Claims, No Drawings

TOPICAL CANNABIDIOL COMPOSITION

RELATED APPLICATIONS

This application claims priority benefit of U.S. Provisional Application Ser. No. 62/910,134 filed 3 Oct. 2019, the contents of which are hereby incorporated by reference.

FIELD OF THE INVENTION

The present invention in general relates to a topical composition, and in particular, to a topical composition containing cannabidiol and to a method for treating chronic pain via application of such a composition to skin at the locus of the chronic pain.

BACKGROUND OF THE INVENTION

The use of both natural and synthetic compounds, such as aspirin, ibuprofen, naproxen, a variety of herbal remedies, corticosteroids, and opioids for the treatment of pain are well known. Although widely used, these compounds cause many negative side effects such as gastric irritation, ulceration, nausea, lowered blood pressure, respiratory depression, itching, and skin rashes.

Chronic pain is generally defined as any pain which lasts more than twelve weeks and often lasts months or even years. In contrast, acute pain is the natural sensation that alerts of the presence of an injury or illness. With acute pain, the pain progressively becomes less severe as the injury heals or illness is fought-off. However, chronic pain exists when pain signals continue to be sent to the brain even after the initial cause of the acute pain is addressed. Chronic pain can also exist wholly without any initial cause of acute pain. Chronic pain one of the most pervasive health problems worldwide. In the United States, chronic pain can affect as many as eight of every ten adults. Common types of chronic pain include headaches, back pain, joint pain, and nerve pain. There is a growing appreciation that the side effect profiles of treatment of chronic pain with over-the-counter analgesics, opioids, and other conventional medications render these as unsuitable for long term pain management options.

The use of cannabis for medical treatment dates back millennia. Archaeological evidence suggests that cannabis was used by many ancient cultures including ancient Chinese, Indo-European, and Egyptian civilizations.

Delta-9-tetrahydrocannabinol (THC) is the primary psychoactive component of cannabis and is known to be an effective treatment for pain. However, THC can also cause adverse psychoactive events depending on dose and patient sensitivity. Cannabinoid receptor type 1 (CB1) and cannabinoid receptor type 2 (CB2) are important signaling pathways for the endocannabinoid system. Psychoactive effects of cannabis are primarily mediated by CB1 which is primarily associated with the central nervous system, whereas CB2 is primarily associated with immune cells. THC has a high affinity for both CB1 and CB2. The high affinity for CB1 causes THC to be the primary psychoactive component of cannabis. In contrast, cannabidiol (CBD) which is a non-psychoactive cannabinoid component of the cannabis plant also known to be an effective treatment for pain, displays minimal affinity for both CB1 and CB2. Thus, CBD is a desirable compound that can be used to treat pain without the risk of adverse psychoactive events inherent with the use of THC.

CBD acts as a partial CB1 antagonist and as a weak inverse CB2 agonist. CBD is also active at other receptors of the endocannabinoid system. Additionally, CBD is active at a variety of other molecular receptors that are not a part of the endocannabinoid system illustratively including agonism at serotonin 1A receptor, vanilloid receptor 1, and adenosine A2A receptors. CBD and has also been observed interacting with other biological systems via indirect chemical mechanisms. These characteristics are believed to play a role in the anti-inflammatory and pain treating properties of CBD.

The endocannabinoid system actively participates in the pathophysiology of osteoarthritis-associated joint pain. The endocannabinoid system also participates in the pathophysiology of chronic pain, including neuropathic pain. Data shows that endocannabinoid receptor agonists such as CBD block pain in various acute and chronic pain models and further act to reduce inflammation via a number of biochemical mechanisms and pathways.

In addition to its anti-inflammatory properties, CBD does not cause the negative side effects caused by common compounds used to treat pain. This makes it an even more attractive alternative for treating pain over common prior art compounds currently in use. Yet, has met with limited acceptance owing to a lack of proper formulation and administration with synergistic substances that improve the efficacy thereof.

Owing to the pervasiveness of both acute and chronic pain worldwide, and the negative side effects caused by common compounds currently used to treat acute and chronic pain, there exists a need for a composition to reduce inflammation and pain that does not cause the negative side effects associated with prior art pain treatment compounds.

SUMMARY OF THE INVENTION

A topical composition is provided that includes cannabidiol (CBD) oil present in an amount of from 5 to 50% total weight and at least one plant extract of wintergreen oil, plai oil (*Zingiber cassumunar*), or *Barleria lupilina* oil. A lipophilic ointment carrier compatible with the CBD oil and the at least one plant extract renders the composition suitable for topical delivery. The at least one anti-inflammation essential oil, and the at least one scented essential oil are dissolved or suspended in a carrier. Vitamin E, or a therapeutically acceptable ester or salt thereof is also provided in some embodiments. In still other embodiments a terpene is added as a a separate component. In still other embodiments, an essential oil is added. The composition is readily applied to the skin as a cream, spray, or impregnated into a topical patch.

A method of treating chronic pain is also provided that includes applying an inventive topical composition to the skin at a locus of the pain and allowing sufficient time for the pain to subside. The composition is applied to the skin of a subject at the locus of pain in a representative treatment course of 1 to 4 times per day for 1 to 8 weeks to reduce pain sensation. The composition is safe and can be used on a regular basis in perpetuity with a regular dosing regimen or a chronic pain flairs.

DETAILED DESCRIPTION OF THE INVENTION

An inventive topical composition and method of treating chronic pain are provided. The inventive topical composition contains cannabidiol (CBD) and plant extract and is well suited to treat chronic pain while also avoiding the negative side effects caused by commonly used anti-inflammatory and pain-treating compounds. As used herein CBD may be derived from natural sources or may be synthetic. When an inventive topical composition is applied to the skin at the locus of pain and allowed sufficient time to absorb, the pain is reduced or even eliminated.

It is appreciated that in addition to the treatment of chronic human pain, an inventive topical composition is readily applied to therapeutic effect to animal skin to treat chronic pain. By way of examples such animals illustratively include dogs, cats, horses, cattle, sheep, primates, or rodents. Inventive compositions also show therapeutic effect on mucosal tissue and internal tissues of humans or animals.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

An inventive topical composition is provided in a lipophilic ointment base or formed into an oil in water emulsion that contains cannabidiol (CBD) oil in an amount of from 5 to 50 total weight percent and at least one plant extract of wintergreen oil (*Gaultheria procumbens*), plai oil (*Zingiber cassumunar*), *Barleria lupilina* oil. In other inventive embodiments CBD oil is present from 16 to 23 total weight percent. In still other embodiments all of wintergreen oil, plai oil, *Barleria lupilina* oil are present. The plant extracts in combination are present from 4 to 44 total weight percent of the composition. In still other embodiments, CBD oil in combination with the at least one plant extract are present in an amount of from 6 to 90 total weight percent of an inventive composition. In other embodiments, the CBD oil and the at least one plant extract are present in a weight ratio of from 0.6-1.7:1.

In inventive embodiments non-limiting examples of synthetically derived cannabidiols illustratively include Lenabasum, CBD-Val-HS, EHP-101, EHP-102, KLS-13019, or combinations thereof; as well as related as cannabigerol.

In inventive embodiments Wintergreen oil extract contains methyl salicylate, pinene, myrcene, δ-3-carene, limonene, 3,7-guaiadiene, and δ-cadinene. A primary metabolite of methyl salicylate is salicylic acid, a proven non-steroidal anti-inflammatory drug. Wintergreen extract has anti-inflammatory and pain-relieving properties and has commonly been used to alleviate arthritic related pain.

Plai oil extract contains 4-terpinenol, sabinene, terpinene, (E)-1-(3,4-dimethoxyphenyl)butadiene, and β-pinene. Plai oil extract has anti-inflammatory properties.

*Barleria lupilina* oil extract contains a variety of tannins, glucosides, phenols, tannins, flavonoids, and terpenoids. *Barleria lupilina* oil extract has anti-inflammatory, anti-arthritic, antimicrobial, and antibacterial properties.

Without intending to be bound to a particular theory, it is believed that the anti-inflammatory properties of CBD can be partially attributed to CBD being an agonist that targets CB2 receptors. Chronic inflammation can lead to chronic pain illustratively including arthritis. Suppressing or inhibiting inflammatory compounds can effectively treat chronic pain. Without intending to be bound to a particular theory, it is believed that endocannabinoids play an active role the pathophysiology of chronic pain including imparting anti-inflammatory effects. It is further believed that the anti-inflammatory properties of CBD can also partially be attributed to CBD's ability to stimulate cannabinoid receptor activity and ability to enhance production and activity of endocannabinoids, catalyzing anti-inflammatory effects. By way of non-limiting example, it is believed that CBD stimulates production and enhances activity of the endogenous cannabinoid ligand anandamide—non-clinically known as the "bliss molecule"—because it reduces or prevents pain sensation. CBD has also been shown to modulate non-endocannabinoid signaling pathways illustratively including inhibition of adenosine uptake which provides increased protection against tissue damage during injury, and stimulation of enhanced activity at serotonin receptors. CBD has also been shown to reduce NO production thereby reducing inflammation. CBD has further been shown to inhibit the expression of inflammatory cytokines and transcription factors. CBD oil in the concentration range of the present invention appears to have synergistic effects with one of the aforementioned plant extracts. Subjects report still better results with the further administration with an essential oil alone or in combination with a non-cananbis derived terpene added separate from the CBD oil. Again, without intending to be bound by a particular theory, it is believed that that oil phase plant extracts have vasodilation properties and solubility in the lipophilic myelin sheath surrounding inflamed nerve cells that interfere with nerve pain signaling.

In some inventive embodiments, an essential oil is provided. The essential oil illustratively includes Peppermint (*Mentha piperita*), Spearmint (*Mentha spicata*), Eucalyptus (*Eucalyptus globulus*), Lavender (*Lavender officinalus*), Orange Blossom (*Citrus sinensis*), Rosemary (*Rosmarinus officinalis*), Aloe (*Aloe vera*), Myrrh (*Commiphora myrrha*), Frankincense (*Boswellia carteri*), Clove (*Syzygium aromaticum*), Chamomile (*Matricaria chamomilla*), Majoram (*Origanum majorana*), Yarrow (*Achillea millefolium*), Sandalwood (*Santalum album*), Ginger (*Zingiber officinale*), Clary Sage (*Salvia sclarea*), Juniper (*Juniperus communis*), Cajuput (*Melaleuca leucadendra*), Camphor (*Cinnamomum camphora*), Cinnamon (*Cinnamomum verum*), and combinations thereof. An essential oil, or combination of essential oils, if present, are present from 0.1 to 19 total weight percent of the composition. Lavender (*Lavender officinalus*) and Orange Blossom (*Citrus sinensis*) appear to be particularly advantageous, each alone, or in combination.

In some inventive embodiments, an inventive topical composition also includes at least one terpene added separate from those found in the CBD oil. By way of reference CBD oil is found to contain in ever decreasing amounts: cannabidiol>myrcene>β-caryophyllene>(E)-β-ocimene.

Terpenes added to an inventive composition illustratively include myrcene, limonene, linalool, menthol, humulene, terpinolene, camphene, terpineol, pinene, beta-caryophyllene, and combinations thereof. In some inventive embodiments, the at least one terpene is sourced from the cannabis plant. Terpenes are known to have a multitude of beneficial medical properties illustratively including anti-inflammatory, muscle relaxant, analgesic, antibiotic, and antimutagenic properties. As such, the presence of at least one terpene into some inventive embodiments of an inventive topical composition increases its efficacy in treating chronic pain. An added terpene or combination thereof, if present, are present from 0.01 to 10 total weight percent of the composition.

By way of non-limiting example, humulene is anti-inflammatory, anti-bacterial, and anti-tumor, and β-caryophyllene is an agonist of CB2 and an anti-inflammatory. Humulene is commonly blended with β-caryophyllene which produces synergistic effects resulting in increased anti-inflammatory and pain treatment efficacy. Without intending to be bound by a particular theory, it is believed that β-caryophyllene, when coupled with CBD, produces increased activity at CB2 and also stimulates the increased production of endocannabinoids catalyzing an anti-inflammatory cascade that increases the efficacy of chronic pain treatment. In certain embodiments of an inventive topical composition, it is further believed that various terpene combinations, when blended with the CBD and various combinations of the at least one plant extract, produce synergistic effects that result in increased anti-inflammatory efficacy thereby increasing the effectiveness of an inventive topical composition in treating chronic pain.

Peppermint extract contains among other constituents menthol (40.7 wt. % of the extract) and menthone (23.4%), menthyl acetate, 1,8-cineole, limonene, beta-pinene carvone, jasmone, carvacrol, limonene, phellandrene, and beta-caryophyllene. Menthol has a pain cessation cooling effect on skin. Peppermint extract also has anti-inflammatory properties.

Spearmint extract contains among other constituents limonene, dihydrocarvone, 1,8-cineol, and menthol. Spearmint extract has anti-inflammatory properties, reduces swelling due to nerve and muscle pain, and reduces pain associated with arthritis.

Eucalyptus extract contains among other constituents 1, 8-cineole pinene, phellandrene, and limonene. 1, 8-cineole is present in an amount of at least 70 total weight percent and confers antibacterial, expectorant, decongestant, and anti-inflammatory properties.

Lavender extract contains linalool, perillyl alcohol, linalyl acetate, camphor, limonene, tannins, triterpenes, coumarins, cineole, and flavonoids. The skin quickly absorbs lavender oil. Lavender extract has anti-inflammatory, antifungal, antibacterial, antiseptic, analgesic, and anxiolytic properties. Lavender extract can also be used as a scenting agent in some embodiments of an inventive topical composition.

Orange blossom extract is made from neroli oil and can also be used as a scenting agent in some embodiments of an inventive topical composition.

Rosemary extract contains cuminic acid, bornyl acetate, caryophyllene, monoterpene hydrocarbons (alpha and beta-pinene), camphene, limonene, camphor, borneol, cineole, linalool, and verbinol. Rosemary contains a wide variety of volatile and aromatic components. Flavonoids in the extract include diosmetin, diosmin, genkwanin, luteolin, hispidulin, and apigenin. Phenols in rosemary extracts include caffeic, chlorogenic, labiatic, neochlorogenic, and rosmarinic acids, as well as salicylates. Without intending to be bound to a particular theory, rosemary extracts in the present invention confer antimicrobial, anti-cancer and anti-oxidative effects. Carnosol and carnosic acid are believed to account for more than 90% of the antioxidant properties of rosemary extract. Rosemary also exhibits anti-inflammatory and pain-relieving properties.

Aloe contains Arachidonic acid, linolenic acid, steroids (campestrol, cholesterol,(3-sitosterol), triglicerides, triterpenoid, glucomannan acemannan, aloeride, gibberillin, lignins, potassium sorbate, salicylic acid, bradykininase, maloyl glucan, veracylglucans, aloe-emodin, and uric acid. Without intending to be bound to a particular theory, aloe present in some embodiments of the present invention confers anti-inflammatory effects. Also, the polysaccharide glucomannan is an effective human skin moisturizer. Acemannan accelerates wound healing. Bradykininase, contributes anti-inflammatory properties and magnesium lactate, antipruritic effects. Salicylic acid and other antiprostaglandin compounds contribute local anti-inflammatory activity. Maloyl glucans also likely act as anti-inflammatories. Veracylglucans confer anti-proliferative effects. Aloe-emodin is thought to inhibit endothelial cell proliferation and inhibits tumor cell proliferation.

Myrrh extract contains myrrholic acid, cinnamic acid, cuminic acid, eugenol, cadinene, pinene, dipentene, heerabolene, limonene, furanodiene-6-one and methoxyfuranoguaia-9-ene-8-one. Without intending to be bound to a particular theory, myrrh extracts present in some embodiments of the present invention confer anti-tumoral effects and anti-microbial effects. Myrrh extract also has cytotoxic, analgesic, and anti-inflammatory properties.

Frankincense extract contains sesquiterpene, camphene, dipentene, pinene, phellandrene, olibanol, boswellic acid (3-alpha-hydroxy-urs-12-en-23-oic acid), volatile oils, terpinols, arabinose, xylose, galactose, uronic acids, beta-sitosterin and phlobaphenes. Without intending to be bound to a particular theory, frankincense extracts in the present invention confer anti-inflammatory effects and include specific inhibitors of 5-lipoxygenase, the key enzyme of leukotriene biosynthesis.

Clove extract contains eugenol, acetyl eugenol, beta-caryophyllene, methyl salicylate, pinene, and vanillin. Clove extract has anti-inflammatory and pain-relieving properties, particularly imparted by the beta-caryophyllene and methyl salicylate.

Chamomile extract contains α-pinene, (β-pinene, sabinene, myrcene, caryophyllene, 1,8-cineol, terpinene, propyl angelate, and butyl angelate. Without intending to be bound to a particular theory, chamomile extracts present in some embodiments of the present invention confer anti-inflammatory and pain-relieving effects.

Majoram extract contains sabinene, alpha-terpinene, gamma-terpinene, cymene, terpinolene, linalool, sabinene hydrate, linalyl acetate, terpineol, and gamma terpineol. Majoram extract has analgesic, antispasmodic, antiseptic, antibacterial, antiviral properties. Majoram also functions as an anxiolytic, expectorant, nervine, sedative, and vasodilator.

Yarrow extract contains tricyclene, alpha-pinene, camphene, beta-pinene, sabinene, borneol acetate, 1,8-cineole, terpinene, limonene, isoartemisia ketone, and borneol. Yarrow extract promotes healing of the skin, reduces swelling in inflamed wounds, and treats gastrointestinal problems. Yarrow extract also has anxiolytic and anti-inflammatory properties.

Sandalwood extract contains sesquiterpenic alcohols including tricyclic alpha-santalol and beta-santalol. Sandalwood extract is an anti-inflammatory.

Ginger extract contains among other constituents camphene, beta-phellandrene, alpha-pinene, geranial, zingiberene, beta-bisabolene, beta-sesquiphellandrene, and curcumene. Ginger extract has anti-inflammatory properties particularly imparted by the camphene, pinene, beta-bisabolene, and curcumene present. Ginger extract is also a bronchodilator, an antioxidant, an antiviral, an antiseptic, and an analgesic.

Clary sage extract contains among other constituents linalyl acetate, linalool, germacrene, alpha-terpineol, and sclareol. Clary sage extract is an anti-inflammatory with a cooling property that soothes skin presenting inflammation. Clary sage extract also promotes wound healing, treats muscle aches, joint pain, and enhances circulation.

Juniper extract contains alpha-pinene, camphene, beta-pinene, sabinene, myrcene, alpha-phellandrene, terpinene, 1,4-cineole, beta-phellandrene, cymene, terpinen-4-ol, bornyl acetate, cayophyllene and trace amounts of limonene, camphor, linalool, linalyl acetate, borneol, and nerol. Juniper extract is an anxiolytic, an anti-inflammatory, treats skin irritation, and promotes fluid retention.

Cajuput extract contains among other constituents viridiflorol and 1,8-cineole. Cajuput extract has anti-inflammatory and pain-relieving properties. It is particularly effective at treating muscle pain.

Camphor extract contains among other constituents alpha-pinene, camphene, limonene, 1,8-cineole and cymene. Camphor extract is an anti-inflammatory and imparts a cooling effect to the skin. It is particularly effective in treating skin irritation such as sores, insect bites, itching, and rashes. It also helps to relieve pain caused by sore muscles. Camphor extract also has antibacterial, antiviral, and antifungal properties. Camphor extract also promotes circulation, has anxiolytic properties, and can reduce the intensity of convulsions, spasms, and muscle contractions.

Cinnamon extract contains among other constituents cinnamaldehyde, cinnamyl acetate, eugenol, and eugenol acetate. The cinnamaldehyde imparts antifungal, antibacterial, and antimicrobial properties. The cinnamyl acetate enhances circulation. The eugenol imparts antiseptic, anti-inflammatory, and analgesic properties. It also can reduce gastric and ulcer related pain. The eugenol acetate imparts antioxidant properties.

In some inventive embodiments, vitamin E, if present, is present from 0.1 to 3 total weight percent. Vitamin E or a derivative thereof has anti-inflammatory properties, promotes wound healing, and treats skin irritation. Vitamin E also boosts immune function, promotes eye health, and may lower the risk of cancer. It is appreciated that Vitamin E esters and salts are operative herein, as detailed in Z.A. Al-Talla and L.T. Tolley, "Analysis of vitamin E derivatives in serum using coordinated ion spray mass spectrometry" Rapid Commun Mass Spectrom. 2005; 19(16):2337-42.

As used herein, a "plant extract" is a concentrated lipophilic pharmaceutical preparation of plants obtained by extraction and concentration of the biologically active constituents therefrom with a suitable solvent. Solvents operative herein include water, $C_1$-$C_{20}$-alcohols, -ethers, -esters, -acids, -alkanes, and -alkenes; and forms thereof containing a substituent. Substituents illustratively include carbonyl-, carboxyl-, amino-, amido-, hydrodroxyl-, and sulfonyl-moieties; and combinations thereof. It is appreciated that elevated temperature plant extractions such as steam-distilled hydrosols are intended to be encompassed herein.

In one inventive embodiment the carrier comprises at least one of petroleum jelly, paraffin, lanolin, menthol, or beeswax. In another embodiment the carrier an inventive topical composition comprises at least one of petroleum jelly, paraffin, menthol, and combinations thereof. In certain embodiments of an inventive topical composition the carrier is in the form of a serum, a cream, a spray, or an ointment. In other inventive embodiments, the inventive topical composition may be in the form of a paste, gel, lotion, powder, aerosol, or liquid. In some inventive embodiments the carrier comprises an oil. Oils suitable for suspension or dissolution of CBD and plant extracts are limited only by storage stability with the CBD and the plant extracts and skin compatibility. Oils operative herein illustratively include plant based oils such as olive oil, grapeseed oil, almond oil, jojaba oil, safflower oil, corn oil, peanut oil, sesame oil, cannola oil, soy oil, soybean oil, burdock root oil, tea tree oil, coconut oil, apricot seed oil, walnut oil, and combination thereof; and animal based oils such as shark liver oil, cod liver oil and fish liver oil; and combinations thereof. In certain inventive embodiments, the carrier oil is selected to operate synergistically with the CBD and the plant extracts by imparting therapeutic properties. By way of non-limiting example apricot kernel oil has the attributes on human skin of being anti-inflammatory and hypoallergenic.

In one embodiment an inventive topical composition comprises at least one of an adjuvant, a steroidal anti-inflammatory such as prototypical cortisone, an anti-bacterial such as silver sols, or a cellular regrowth stimulating substance such as biotin or epidermal growth factor. Illustrative examples of acceptable adjuvants include waxes; paraffins; starch; tragacanth; a pluronic; cellulose and cellulose derivatives; silicones; bentonites; silicic acid; talc; zinc oxide; aluminum hydroxide; calcium silicates; alginate; acrylate; hyaluronic acid; polyethylene glycol; vitamins such as ascorbic acid glucosides; partial glycerides of fatty acids; chitosan; and mixtures thereof.

In addition, some embodiments of the inventive topical composition may contain one or more compounds for improving cosmetic acceptability, including but not limited to, preservatives, humectants, fragrances, coloring agents, emollients, fillers, and the like.

A preservative is included in some inventive compositions at a concentration effective to inhibit undesirable effects such as microbial growth, UV and/or oxygen-induced breakdown of composition components, and the like. A preservative operative in an inventive gel is any of those known in the art and compatible with the components of an inventive composition. Examples include butylated hydroxytoluene (BHT) used as an antioxidant and edetate disodium (EDTA) used as an antioxidant synergist. When a preservative is included, it is present at concentrations sufficient to confer a preservative effect. In the case of BHT the typical range is from 0.01 to 0.03% and in the case of EDTA the typical range is from 0.005 to 0.1%.

A humectant has emollient properties. Humectants operative herein illustratively include glycerin, capric/caprylic triglyceride, vegetable oils, *Aloe barbadensis*, and combinations thereof. A humectant is included at concentrations ranging from 0 to 10 total weight percent.

The preparation of the composition according to the invention includes bringing the CBD and constituent plant extracts together in determined and precise proportions and in determined and precise forms, and this causes a synergy in therapeutic effect as to treating chronic pain. The inventive topical composition obtained gives effects and results which are considerably improved in comparison with the effects and results obtained with each constituent taken in isolation and successively or in a cumulative manner, and this is unexpected and surprising based on the prior art. The inventive composition also gives these improved effects and results without the negative side effects commonly experienced with prior art chronic pain treatments.

Because the inventive topical composition is applied to compromised skin in some inventive embodiments, all or some of the constituents of certain embodiments of an inventive composition are sterilized, either individually or together. Any suitable sterilization method or combination of sterilization methods can be used and can be used on any combination of composition and/or packaging components, as long as the sterilization does not adversely affect the therapeutic effectiveness of the inventive topical composition. By way of non-limiting example, suitable sterilization techniques that may be employed include dry and moist heat sterilization, ionizing radiation (such as electron beam or gamma irradiation), exposure to gas, and aseptic filtration. It is appreciated that heat sterilization has a propensity to damage many plant extract components such as carbohydrates and proteins and as a result should be used with caution to avoid the loss of therapeutic effect. Where one or more of the above-described additives are present in the inventive composition, and where the other components of the composition are sterilized as described above, it is preferred that the additional additives also be sterilized as described above, so that sterility of the entire composition can be maintained.

In some inventive embodiments, a skin penetration enhancer is present from among propylene glycol, benzyl alcohol, and 2-(2-ethoxyethoxy)ethanol and are each individually typically present in amounts of from 0% to 10% of the total weight of the composition. Without intending to be bound to a particular theory, these enhancers solvate CBD oil components and transport the active compounds of the present invention through the stratum corneum. This lipophilic nature of a CBD oil, the plant extracts, and a skin penetration enhancer is seen as a positive quality in skin penetration and pain relief. Skin penetration enhancers are appreciated to be particular useful in transdermal patches impregnated with an inventive composition to provide sustained dosing to a locus of pain.

Compositions for administration as aerosols are prepared by dissolving CBD oil and the aforementioned plant extracts in an amount of up to 15% total weight percent in the ratios as detailed above in a solvent such as ethanol, propanol or isopropanol, and mixing therewith a volatile propellant, and placing the mixture in a pressurized container having a metering valve to release the mixture with an aerosol droplet size.

The liquefied propellant employed typically is one which has a boiling point below ambient temperature at atmospheric pressure. For use in compositions intended to produce aerosols for medicinal use, the liquefied propellant should be non-toxic.

Among the suitable liquefied propellants which can be employed are the lower alkanes containing up to five carbon atoms, such as butane and pentane, or an alkyl chloride, such as methyl, ethyl or propyl chlorides. Further suitable liquefied propellants are the $C_1$-$C_4$ fluoralkanes or $C_1$-$C_4$ fluorochloroalkanes. Exemplary propellants are tetrafluoroethane and heptafluoropropane.

The aerosol sprays are made by nebulizing the solution containing active CBD oil and plant extract compound, using a variety of known nebulizing techniques. The aerosol system has a solution of the active compounds, and other therapeutic agents, if desired, in a liquid propellant. Both liquid and vapor phases are present in a pressurized container and when a valve on the container is opened, liquid propellant containing the dissolved compounds is expelled as an aerosol mist that is readily aimed at the target locus of pain.

An inventive topical composition may be applied to the skin at a locus of the pain. In certain inventive embodiments chronic pain will begin to subside within fifteen minutes of applicating of an inventive topical composition to the skin at a locus of the pain. In some inventive embodiments a single application of an inventive topical composition maintains therapeutic effect for up to three hours. For further protection and to ensure the inventive composition is fully absorbed into the skin, it is appreciated that a covering is readily applied over the skin covered by the inventive composition. Any suitable covering may be used, and may be tailored to the location, type, and severity of the chronic pain. By way of illustrative example, suitable coverings include bandages, wound dressings, gloves, and the like. In certain inventive embodiments a transdermal patch is impregnated with an inventive composition. The transdermal patch impregnated with an inventive composition is affixed to the skin at a locus of the pain.

To prepare an inventive composition, the CBD and the plant extracts are prepared by conventional methods or purchased commercially. In certain inventive embodiments, at ambient temperature, the CBD and the plant extracts are added to a prepared carrier and additional stirring performed as needed.

The present invention is further detailed with respect to the following non-limiting examples and comparatives.

EXAMPLES

Example 1

CBD oil is produced based on a method of T.A. Attard et al. "Utilisation of supercritical fluids for the effective extraction of waxes and Cannabidiol (CBD) from hemp wastes", Ind. Crops and Products, 112; 2018; 38-46 in which 100 g of blender macerated hemp leaf is placed in a Soxhlet apparatus. This was fitted to a 4 L round bottom flask containing heptane (1 L). The solution refluxes for 4 hours. The resulting solution is filtered and lyophilized to obtain CBD oil. The resulting CBD oil has a composition by weight percent of cannabidiol (61%), myrcene (22%), β-caryophyllene (13%), and (E)-(β-ocimene (3%). The δ-9-tetrahydrocannabinol (THC) is present at a level of less than 1%.

Comparative Example A

A cohort of 40 subjects with an age range of between 35 and 60, both male and female, each of the subjects suffering chronic pain over the joints of the hand and also suffered muscle pain is instructed to apply cream of 20 total weight percent CBD oil in a petrolatum carrier three times daily for six weeks. After the six-week period, 40% of the subjects reported anecdotal improvement.

Comparative Example B

A cohort of 40 subjects with an age range of between 35 and 60, both male and female, each of the subjects suffering chronic pain over the joints of the hand and also suffered muscle pain is instructed to apply cream of 1 total weight percent CBD oil in a petrolatum carrier three times daily for six weeks. After the six-week period, only one of the subjects reported anecdotal improvement.

Example 2

Another cohort of 40 subjects with an age range of between 35 and 60, both male and female, each of the subjects suffered chronic pain over the joints of the hand and also suffered muscle pain. Each subject was instructed to apply a cream of 20 total weight percent CBD oil, 5 total weight percent of wintergreen oil, 5 total weight percent of plai oil (*Zingiber cassumunar*), and 5 total weight percent of *Barleria lupilina* oil in a petrolatum carrier. After the six-week period, 100% of the subjects reported anecdotal improvement with an onset of therapeutic effects occurring within 15 minutes of application of the inventive topical composition and lasting up to three hours with a single application. Subsequent applications were also reported to provide therapeutic effects within 15 minutes of application of the inventive topical composition and also to last up to three hours. Thus, no tolerance build-up to the inventive composition was observed. No adverse events or significant adverse events were observed.

Example 3

The test of Example 2 is repeated with 10 like situated subjects applying a cream of 20 total weight percent CBD oil, 15 total weight percent of plai oil (*Zingiber cassumunar*) in a petrolatum carrier. Like levels of improvement are noted compared to Example 2.

Example 4

The test of Example 2 is repeated with 10 like situated subjects applying a cream of 20 total weight percent CBD oil, 5 total weight percent of wintergreen oil, 5 total weight percent of plai oil, and 5 total weight percent of *Barleria lupilina* oil and further containing 3 total weight percent of lavender oil and 1 total weight percent orange blossom oil in a petrolatum carrier. Like levels of improvement are noted compared to Example 2 with the further report of quicker onset of relief.

Example 5

The test of Example 2 is repeated with 10 like situated subjects applying a cream of 20 total weight percent CBD oil, 5 total weight percent of wintergreen oil, 5 total weight percent of plai oil, and 5 total weight percent of *Barleria lupilina* oil and further containing 3 total weight percent menthol in a petrolatum carrier. Like levels of improvement are noted compared to Example 2 while some found the added cooling sensation associated with the menthol helpful while others found this sensation irritating.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A topical composition comprising:
cannabidiol (CBD) oil or synthetic derivative thereof present in an amount of from 5 to 50% total weight percent;
wintergreen oil and *Barleria lupulina* oil, and optional plai oil, said wintergreen oil and said *Barleria lupulina* oil and said optional plai oil in sum present in an amount of from 16 to 44% total weight percent of the composition and comprising tannins, glucosides, phenols, flavonoids, and terpenoids present and imparting anti-inflammatory, anti-arthritic, antimicrobial, and antibacterial properties to the topical composition, said *Barleria lupulina* oil and said optional plai oil, present in an amount of at least 10 total weight percent; and
an oil containing carrier compatible of at least one of petroleum jelly, paraffin, coconut oil, or lanolin in which said wintergreen oil and said *Barleria lupulina* oil and said optional plai oil are dissolved to form an ointment.

2. The topical composition of claim 1 wherein said cannabidiol (CBD) oil is present in an amount of from 10 to 25 total weight percent.

3. The topical composition of claim 1 wherein said cannabidiol (CBD) oil is present in an amount of from 16 to 23 total weight percent.

4. The topical composition of claim 1 wherein said plai oil is present.

5. The topical composition of claim 1 further comprising vitamin E, or a therapeutically acceptable ester or salt thereof.

6. The topical composition of claim 1 further comprising at least one terpene added as a separate component.

7. The topical composition of claim 6 wherein said at least one terpene is selected from the group consisting of: menthol, myrcene, limonene, linalool, humulene, terpinolene, camphene, terpineol, pinene, beta-caryophyllene, and combinations thereof.

8. The topical composition of claim 1 further comprising an essential oil.

9. The topical composition of claim 8 wherein said essential oil is selected from the group consisting of: peppermint, spearmint, eucalyptus, rosemary, aloe, myrrh, frankincense, clove, chamomile, marjoram, yarrow, sandalwood, ginger, clary sage, juniper, cajuput, camphor, cinnamon, or combinations thereof.

10. The topical composition of claim 1 wherein said CBD oil in combination with said *Barleria lupulina* oil and optional plia oil are present in an amount of from 10 to 90 total weight percent.

11. The topical composition of claim 1 further comprising at least one of an adjuvant, a steroidal anti-inflammatory, an anti-bacterial, or a cellular regrowth stimulating substance.

12. The topical composition of claim 1 further comprising a skin penetration enhancer.

13. The topical composition of claim 1 wherein the synthetic derivative is present and selected from the group consisting of Lenabasum, CBD-Val-HS, EHP-101, EHP-102, and KLS-13019.

14. A topical composition comprising:
cannabidiol (CBD) oil or a synthetic derivative thereof present in an amount of 16 to 23 total weight percent;
anti-inflammation essential oil of wintergreen oil, *Barleria lupulina* oil, and optional plai oil present in sum in an amount of from 16 to 44% total weight percent of the composition and comprising tannins, glucosides, phenols, flavonoids, and terpenoids present and imparting anti-inflammatory, anti-arthritic, antimicrobial, and antibacterial properties to the topical composition, said *Barleria lupulina* oil and said optional plai oil, present in an amount of at least 10 total weight percent;
at least one scented essential oil of lavender oil or orange blossom oil; and
a lipophilic ointment carrier compatible of at least one of petroleum jelly, paraffin, coconut oil, or lanolin in which said CBD oil, said at least one anti-inflammatory essential oil, and said at least one scented oil are dissolved to form an ointment.

15. A method of treating chronic pain in a subject comprising:
applying the topical composition of claim 1 to the skin of the subject at a locus of the pain; and
allowing sufficient time for the pain to subside.

16. The method of claim 15 further comprising applying a bandage over the topical composition after the applying and in contact with the skin.

17. The method of claim 16 further comprising impregnating a transdermal patch with the topical composition and the applying being from the transdermal patch.

18. The method of claim 17 further comprising further secondary applying the topical composition two additional times in a 24-hour period.

\* \* \* \* \*